United States Patent
Mendes et al.

(10) Patent No.: US 9,187,410 B2
(45) Date of Patent: Nov. 17, 2015

(54) PROCESS FOR ISOLATING TIGECYCLINE AND TIGECYCLINE MADE THEREFROM

(75) Inventors: Zita Mendes, Lisbon (PT); Guy Villax, Lisbon (PT)

(73) Assignee: Hovione Inter Limited, Lucerne (CH)

( * ) Notice: Subject to any disclaimer, the term of this patent is extended or adjusted under 35 U.S.C. 154(b) by 0 days.

(21) Appl. No.: 13/145,445

(22) PCT Filed: Jan. 22, 2010

(86) PCT No.: PCT/GB2010/000104
§ 371 (c)(1),
(2), (4) Date: Oct. 18, 2011

(87) PCT Pub. No.: WO2010/084325
PCT Pub. Date: Jul. 29, 2010

(65) Prior Publication Data
US 2012/0028928 A1 Feb. 2, 2012

(30) Foreign Application Priority Data
Jan. 23, 2009 (PT) .......................... 104350

(51) Int. Cl.
A61K 31/65 (2006.01)
A61P 31/00 (2006.01)
B29B 9/16 (2006.01)
C07C 231/24 (2006.01)
C07C 237/26 (2006.01)

(52) U.S. Cl.
CPC ............ *C07C 231/24* (2013.01); *A61K 31/65* (2013.01); *C07C 237/26* (2013.01); *C07C 2103/46* (2013.01)

(58) Field of Classification Search
USPC ...................... 552/203, 205; 264/12; 514/152
See application file for complete search history.

(56) References Cited

U.S. PATENT DOCUMENTS

| 5,494,903 | A | 2/1996 | Hlavka et al. | |
|---|---|---|---|---|
| 5,675,030 | A | 10/1997 | Krishnan et al. | |
| 7,790,905 | B2 * | 9/2010 | Tawa et al. | 548/375.1 |
| 7,927,613 | B2 * | 4/2011 | Almarsson et al. | 424/400 |
| 7,947,741 | B2 * | 5/2011 | Bostian et al. | 514/637 |
| 8,067,414 | B2 * | 11/2011 | Garvey | 514/236.2 |
| 8,198,469 | B2 * | 6/2012 | Tsiperman et al. | 552/205 |
| 8,263,645 | B2 * | 9/2012 | Keller | 514/456 |
| 8,529,914 | B2 * | 9/2013 | Fuisz et al. | 424/400 |
| 8,679,527 | B2 * | 3/2014 | Keiji et al. | 424/447 |
| 9,072,679 | B2 * | 7/2015 | Heggie et al. | 1/1 |
| 2005/0031692 | A1 * | 2/2005 | Beyerinck et al. | 424/486 |
| 2007/0026080 | A1 | 2/2007 | Chanana et al. | |
| 2007/0123497 | A1 | 5/2007 | Krishnan et al. | |
| 2008/0090789 | A1 | 4/2008 | Tsiperman et al. | |
| 2009/0275766 | A1 | 11/2009 | Pozzi et al. | |
| 2011/0124893 | A1 * | 5/2011 | Decristoforo et al. | 552/205 |

FOREIGN PATENT DOCUMENTS

| EP | 2116525 A1 | 11/2009 |
|---|---|---|
| WO | 96/18647 A1 | 6/1996 |
| WO | 2006/138641 A2 | 12/2006 |
| WO | 2007/098500 A2 | 8/2007 |
| WO | 2008066935 A2 | 6/2008 |
| WO | 2008102161 A2 | 8/2008 |
| WO | 2009092680 A2 | 7/2009 |

OTHER PUBLICATIONS

Broadhead, J. et al. (Drug development and Industrial Pharmacy, 18(11&12), 1169-1206 (1992).*
Reverchon et al. (J. of Supercritical Fluids 26 (2003) 243-252).*
PCT International Preliminary Report on Patentability, PCT/GB2010/000104 filed Jan. 22, 2010, dated Jun. 5, 2011.
Yu, L. "Amorphous Pharmaceutical Solids: Preparation, Characterization and Stabilization," Advanced Drug Delivery Reviews, May 16, 2001, vol. 48, No. 1, pp. 27-42.
Greer, "Tigecycline (Tygacil): the first in the glycylcycline class of antibiotics", Pharmacology Notes, Baylor University Medical Center Proceedings, vol. 19, No. 2, pp. 155-161.
Columbano et al., "A study of crystallisation of amorphous and salbutamol sulphate using water vapour sorption and near infrared spectroscopy", International Journal of Pharmaceutics, 2002, vol. 237, pp. 171-178.
Greer, "Tigecycline (Tygacil): the first in the glycylcycline class of antibiotics", Proceedings (Baylor University. Medical Center), 2006, vol. 19, pp. 155-161.
Injac et al., "Thermostability Testing and Degradation Profiles of Doxycycline in Bulk, Tablets, and Capsules by HPLC", Journal of Chromatographic Science, 2007, vol. 45, pp. 623-628.
Liang et al., "Stability studies of tetracycline in methanol solution", Journal of Chromatography A, 1998, vol. 827, pp. 45-55.

* cited by examiner

*Primary Examiner* — Sabiha N Qazi
(74) *Attorney, Agent, or Firm* — MacMillan, Sobanski & Todd, LLC

(57) ABSTRACT

The present invention provides a process for isolating tigecycline which process comprises the step of spray drying a solution of tigecycline in a solvent. Preferably the solvent is water or an organic solvent. In another aspect, there is provided tigecycline obtainable by spray drying, particularly in amorphous form. In particular, the invention provides tigecycline obtainable by spray drying according to the process of the invention.

10 Claims, 7 Drawing Sheets

Fig. 1 – XRPD of spray dried tigecycline

Fig. 2 —Comparison of the two reversible heat flow mDSC curves
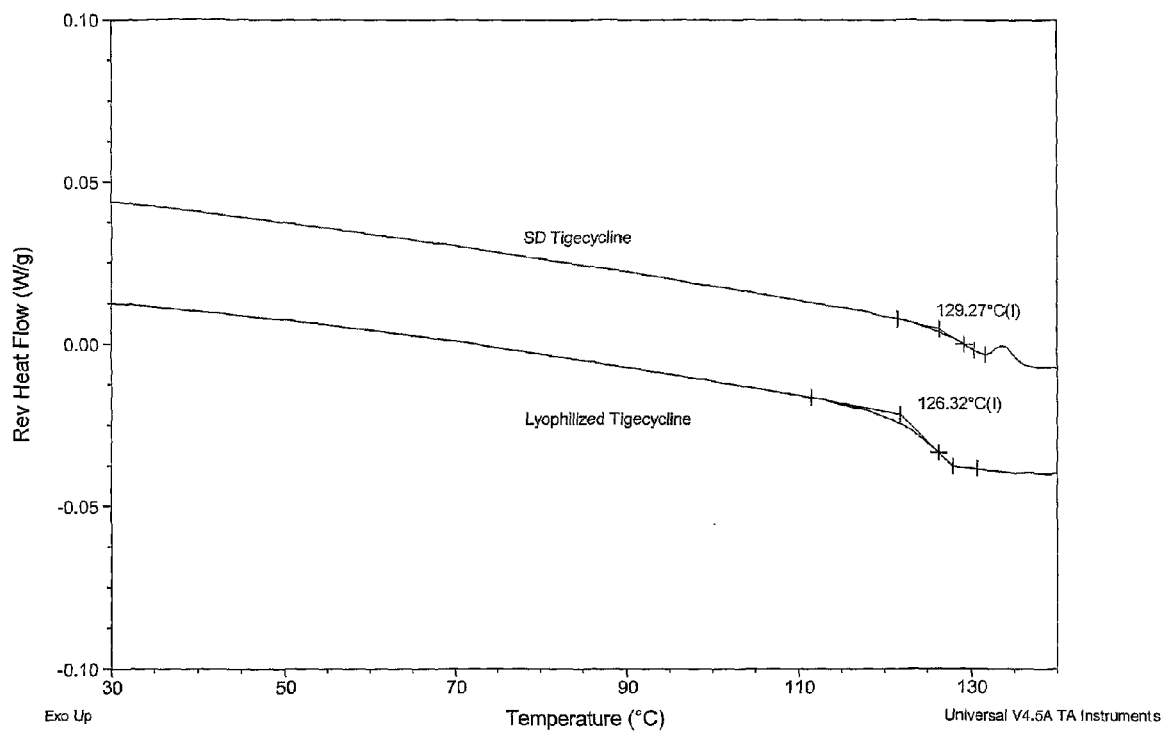

Fig. 3 – Comparison of the total heat flow DSC curves of spray drying tigecycline and lyophilized tigecycline
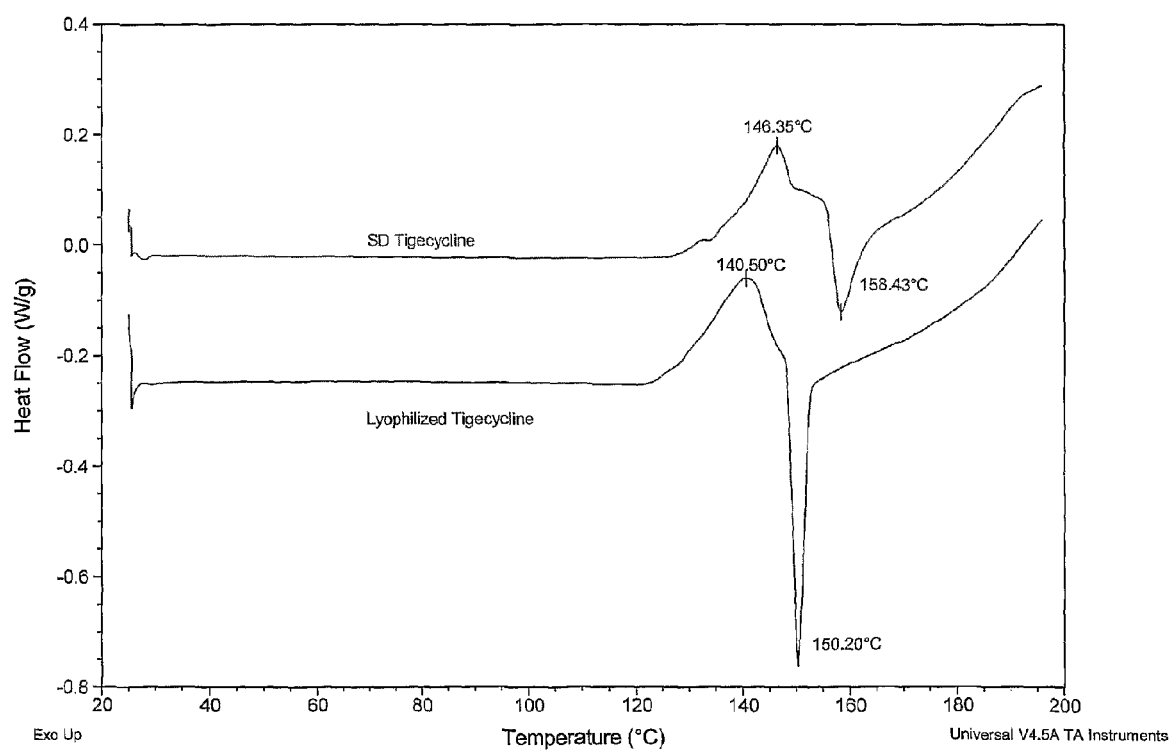

Fig. 4 –Comparison of the two reversible heat flow mDSC curves after 24 hours at 100 °C.
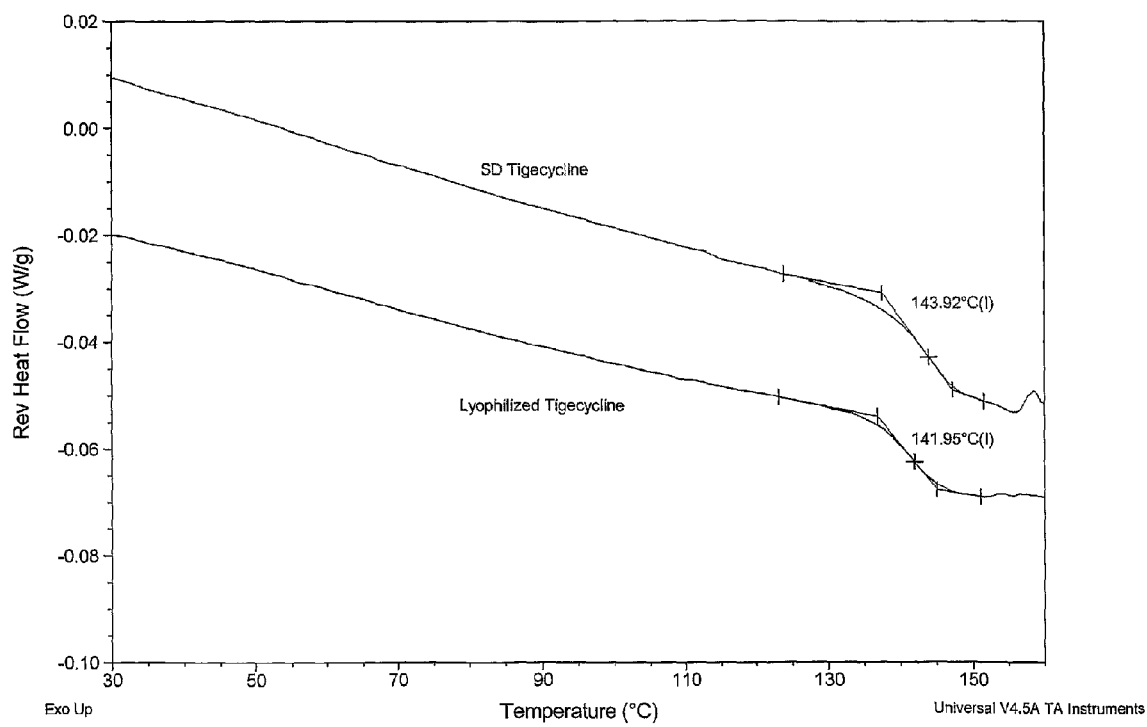

Fig. 5 – Comparison of the total heat flow of spray dried tigecycline and lyophilized tigecycline after 24 hours at 100 °C.
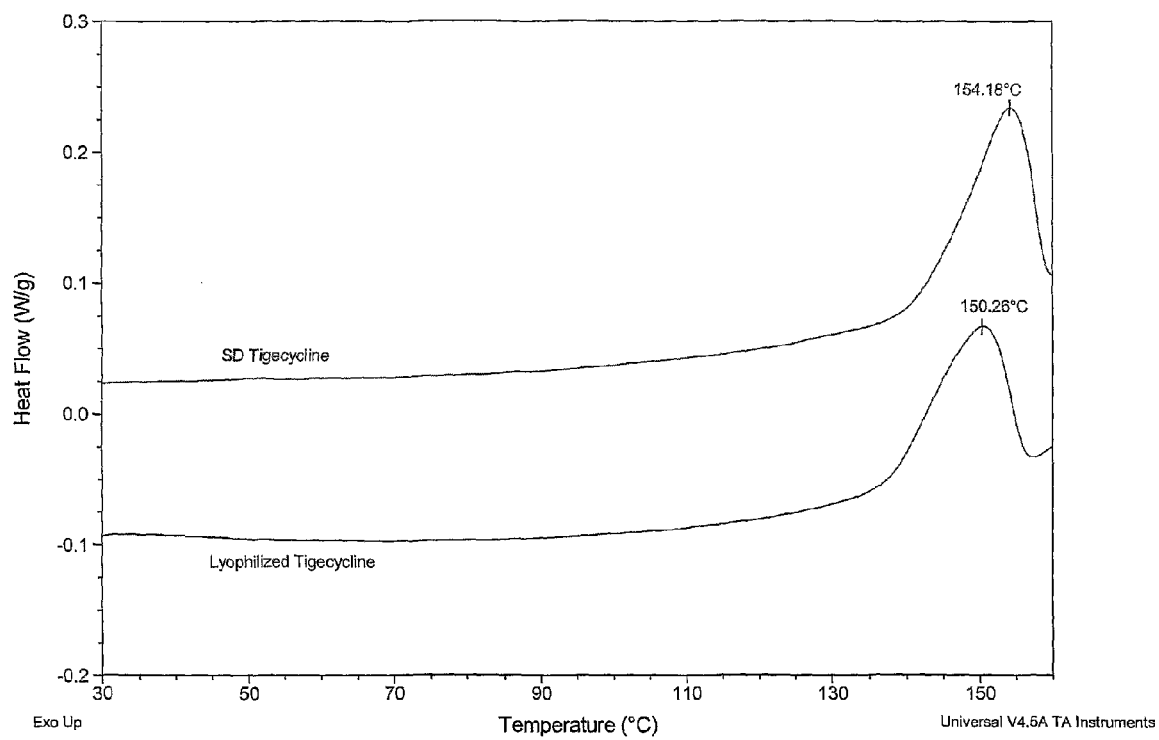

Fig.6 – Adsorption/desorption isotherm comparison profile of spray dried and lyophilised tigecycline. Weight change is with regard to the dried weight
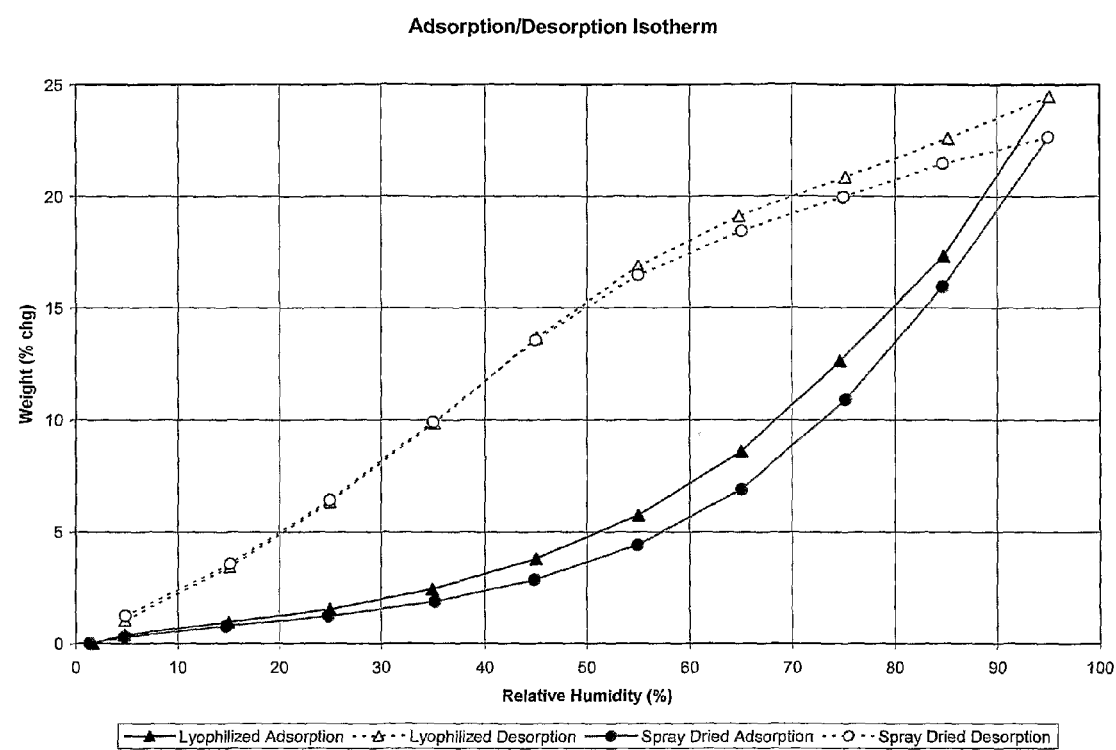

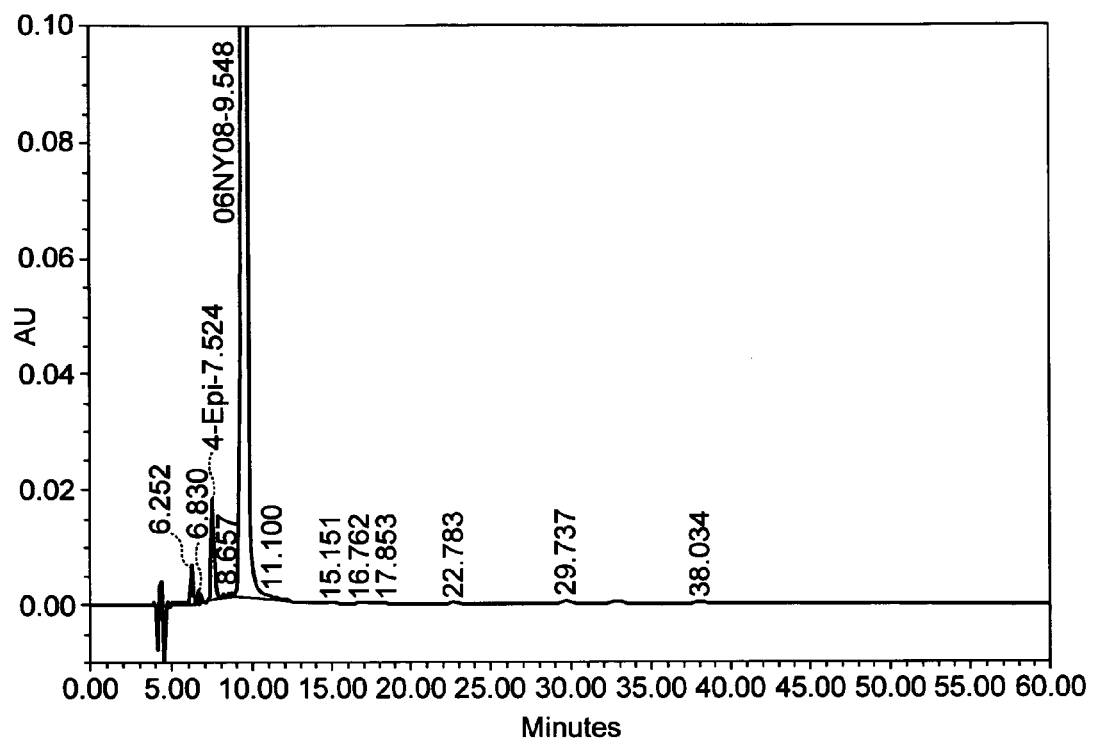
Fig. 7 HPLC chromatogram of spray dried tigecycline

PROCESS FOR ISOLATING TIGECYCLINE AND TIGECYCLINE MADE THEREFROM

This application claims the benefit of the PCT/GB2010/000104 filed Jan. 22, 2010, which claims priority to the PT-104350 application filed Jan. 23, 2009, the entire disclosures of which are expressly incorporated herein by reference.

The present invention relates to an improved process for isolating tigecycline, and to tigecycline made therefrom. The present process is particularly useful for preparing the compound on an industrial scale.

The method according to the present invention is superior to the known prior art methods. Unexpectedly and surprisingly, a more stable amorphous form of tigecycline with a low content of impurities can be obtained by applying the method described.

This isolation process disclosed in this invention is easily scaled up and can be applied at industrial scale.

Tigecycline is the first marketed glycylcycline, a broad spectrum minocycline derivative antibiotic that has demonstrated efficacy for the treatment of complicated skin and skin structure infections and complicated intra-abdominal infections. It has shown remarkable in vitro activity against a wide variety of gram-positive, gram-negative and anaerobic bacteria including many multidrug resistant strains.

Tigecycline has been introduced by Wyeth under the brand name of Tygacyl®, received Food and Drug Administration (FDA) approval in 2005 and has been marketed in the United States since June 2006.

Since it has only poor bioavailability, only IV applications are used.

It is currently presented as a sterile, lyophilized powder for intravenous injections.

Temperature and oxygen levels have to be monitored in the entire manufacturing process in order to control epimer formation and degradation by oxidation.

The stability of the amorphous material used to prepare intravenous injections is a key parameter.

We have now found that, surprisingly, a more stable amorphous material compared with the lyophilized product is obtained when the isolation is made by spray drying.

Tigecycline is disclosed in U.S. Pat. No. 5,494,903, a product patent, while a process for its preparation is disclosed in U.S. Pat. No. 5,675,030.

The chemical structure of tigecycline is shown as formula [1]

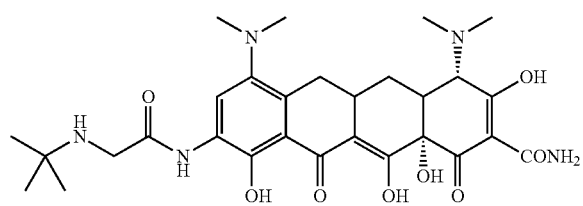

U.S. Pat. No. 5,675,030 mentions the isolation of solid tigecycline by evaporation of a dicloromethane solution. The tigecycline obtained by this isolation method is amorphous.

US 2007/0026080 describes a lyophilizing process to obtain a powder for reconstitution in a vial.

US 2009/0275766 discloses a freeze dying process for amorphous tigecycline. Anti-solvent precipitation and nebulisation methods are also mentioned.

WO 2008/066935 also describes two ways of preparation of amorphous forms of tigecycline:
  via slurry in methyl acetate
  via precipitation—tigecycline is completely dissolved in methyl iso-butyl ketone and upon addition of n-heptane, precipitation takes place.

US2007/0123497, US2008/090789 and WO2008/066935 disclose different crystalline forms of tigecycline.

According to one aspect of the present invention, there is provided a process for isolating tigecycline which process comprises the step of spray drying a solution of tigecycline in a solvent. Preferably the solvent is water or an organic solvent.

In another aspect, there is provided tigecycline obtainable by spray drying. In particular, the invention provides tigecycline obtainable by spray drying according to the process of the invention.

The invention also provides amorphous tigecycline obtainable by spray drying.

In another aspect, there is provided a pharmaceutical formulation comprising tigecycline according to the invention and a pharmaceutically acceptable carrier therefor. Preferably, the formulation is an IV formulation.

There is also provided tigecycline according to the invention for use as a medicament.

In particular, the tigecycline of the invention may be for use in treating skin or abdominal, including intra-abdominal, infections.

The present invention provides amorphous solid, obtainable by a process comprising spray drying of a solution of tigecycline.

Advantageously, the isolation process disclosed in the present invention, gives a more stable amorphous material than the product obtained by freeze dried or by evaporation of the solvent.

Tigecycline can be dissolved in any suitable solvent, provided that the solvent is capable of adequately dissolving the compound. For example, water or a convenient organic solvent may be used. Suitable solvents include dichloromethane; C1 to C4 esters such as ethyl acetate; an alcohol, for example a C1 to C4 alcohol, such as methanol, ethanol, propanol or butanol; and tetrahydrofuran. Preferably, the solvent is such that it can be safely evaporated in the spray drying equipment.

Any suitable tigecycline concentration can be used in the solution. However a solution concentration from about 2% to about 28% w/w is preferred. A more preferred range is from about 8% to about 22% w/w, and ideally a concentration of about 10% w/w is used. Other preferred concentration ranges include from 2% to 19%, and from 5% to 15% (all by w/w). By "% w/w" we mean the mass of the compound of formula [1] as a percentage of the mass of the total solution. The concentration to be employed will generally be determined by the solubility of [1] in the solvent of choice, as will be clear to the skilled addressee.

Spray drying may be performed using any suitable and commercially available equipment.

A variety of atomization methods can be used, depending on the equipment being used. For example a pneumatic spray nozzle orifice of 0.7 mm is suitable although alternative atomization methods such as rotary, pressure and ultrasonic nozzles can be used.

The preferred atomization gas flow (ie the flow rate of the hot gas used in the drying chamber) in terms of normal liters per hour can be adjusted according to the equipment used and any suitable atomization gas flow can be used. Typically, particularly for a smaller scale unit, about 300 to about 670 liters per hour is preferred. In a preferred embodiment, the nozzle assembly can be cooled with a suitable fluid during spray drying to minimize product degradation.

Preferably, the hot gas used for drying excludes the presence of oxygen. In one embodiment, the gas comprises pure nitrogen.

For the spray drying, any suitable drying temperature can be used. The temperature at the outlet of the main drying chamber (the "outlet temperature") can, for example, be varied. Preferably, the outlet temperature (and thus the drying temperature in the chamber) range is from about 60° C. to about 110° C., more preferably from about 70 to about 90° C. A temperature of about 80° C. is particularly suitable.

The inlet temperature (ie the temperature at the inlet of the main drying chamber) may be adjusted to attain the desired outlet (and thus drying) temperature.

Any suitable solution flow rate can be used for the tigecycline solution during spray drying. The solution flow rate is preferably from about 1 to about 20 ml/min, more preferably from about 3 to about 9 ml/min for a 0.7 mm nozzle.

In a particularly preferred embodiment, the outlet temperature, atomization flow rate, solution concentration and solution flow rate, among other tested parameters, are each controlled within the preferred ranges given and are combined so as to obtain compound [1] with a suitable quality.

Preferably, the process is carried out using "Aseptic spray drying", which, as will be known to those skilled in the art, is a spray drying process where all the steps are done in an aseptic way, so as to avoid contamination of the product by, for example, outside microbiological agents.

The compound [1] obtained using the method of this invention is an amorphous solid. However, and shown further below, it has different physical characteristics when compared to the known lyophilised form, and in particular is a more stable amorphous form. It is believed that these differences in the final product are attributable to the process used.

The X-ray powder diffraction pattern (XRPD) of tigecycline obtained by spray drying according to the process herein disclosed is presented in FIG. 1.

The XRPD diffraction pattern presents halos which are characteristic of an amorphous material.

The XRPD apparatus used was an X-Pert-Pro from PANalytical with the following settings: configuration=reflection transmission spinner; scan range: 3.0000-49.9921; step size: 0.0167; n° of points: 2812; counting time: 50.165.

Modulated differential scanning calorimetry (mDSC) of the amorphous compound of formula [1] obtained by spray drying shows a glass transition temperature (Tg) of 129° C. while lyophilized compound of formula [1] has a glass transition temperature of 126° C.

FIG. 2 shows the reversible heat flow mDSC curves of the two products.

The DSC apparatus used was a DSC Q200 from TA Instruments, using the following settings: method—from 25° C. to 300° C. at 3° C./min; modulate +/−0.50° C. every 40 seconds.

In addition to a higher Tg value, spray dried tigecycline also crystallizes and melts (after crossing the glass transition) at higher temperature than lyophilized tigecycline. By Tg we mean the critical temperature at which the material changes its behaviour from being 'glassy' to being 'rubbery'. 'Glassy' in this context means hard and brittle (and therefore relatively easy to break), while 'rubbery' means elastic and flexible.

FIG. 3 illustrates this behaviour and shows the total heat flow DSC curves for the two products. The crystallisation and melting temperatures of the spray dried form are about equal to or greater than 146° C. and 158° C. respectively.

Surprisingly, this behavior indicates a greater stability of the amorphous form obtained by spray drying when compared to the form obtained by lyophilization.

Spray dried tigecycline and lyophilized tigecycline were submitted to fast stress conditions by placing the samples in an oven at 100° C. for 24 hours.

The reversible and total flow DSC curves for the stressed samples were then measured and the results are presented in FIG. 4 and FIG. 5 respectively.

As previously shown in FIGS. 2 and, 3; FIGS. 4 and 5 illustrate that spray dried tigecycline also has higher glass transition and crystallization temperatures (equal to or greater than about 143° C. and 154° C. respectively) after 24 hours at 100° C. compared to the lyophilised form.

This reinforces the greater stability of the amorphous form obtained by spray drying when compared to amorphous form obtained by lyophilization.

We also have performed Dynamic Vapour Sorption studies (DVS) and these studies have shown that samples of tigecycline isolated by spray drying and by lyophilzation have distinctive hygroscopic behavior.

In particular, the amorphous material obtained by lyophilization takes up more water than the amorphous material isolated by spray drying. This behavior suggests differences in the physicochemical proprieties of spray dried and lyophilized tigecycline and reinforces the view that they are different forms of the compound.

FIG. 6 shows the adsorption/desorption isotherm comparison profile of the two samples: amorphous material from spray drying and amorphous material from lyophilization.

Moisture sorption isotherms of active pharmaceutical ingredients (APIs) are used for evaluation of their stability and processing requirements.

The DVS conditions were as follows: temperature-25° C.; equilibrium criteria 0.00% w/w every 10 min; maximum equilibrium time—120 min; start RH—5%; maximum RH—95%; steps—10%. A vapor sorption analyzer (VTI-SGA 100) was used.

As can be seen in FIG. 6, the spray dried sample takes up less water than lyophilized tigecycline. The difference in the water uptake between the two forms increases with RH for most of the isotherm. By RH we mean relative humidity, the amount of water vapor that exists in a gaseous mixture of air and water.

At 45% humidity, the spray dried sample takes up 2.9% w/w water and lyophilized sample 3.9% w/w water. At 95% humidity, the difference is even more evident: the spray dried form takes up 22.6% w/w water and the lyophilized form 24.5% w/w water. The form obtained by lyophilization is more hygroscopic than the form obtained by spray drying. This indicates the lyophilised form is less stable and this will likely have implications for short and long term stability, particularly when used in pharmaceutical formulations.

Suitable pharmaceutical formulations using tigecycline provided by the present invention can be provided in a conventional way using appropriate pharmaceutically acceptable excipients, as will be clear to those skilled in the art. For example, IV formulations for infusion or injection can be provided by mixing amorphous tigecycline powder with an aqueous solution of sodium chloride (eg 9 mg/ml or 0.9% solution) or an aqueous dextrose solution (eg 50 mg/ml or 5% solution) to give a 10 mg/ml solution of tigecycline, which can then be further diluted, for instance, in an infusion bag (eg 5 ml in 100 ml bag) containing a compatible intravenous solution. Suitable excipients include lactose and hydrochloric acid and sodium hydroxide for tonicity and pH adjustment, as will be clear to those in the art.

Example 1 is set forth to aid in understanding the invention but not intended to, and should not be considered as to, limit its scope in any way. The experiment reported was carried out using a BUCHI model B-290 Advanced spray dryer.

EXAMPLE 1

Spray Drying of Tigecycline

Purified tigecycline was obtained by applying literature techniques.

Tigecycline (16 g) was dissolved in water to give a 10% w/v solution.

The outlet temperature was kept between 75° C. and 85° C., the atomization flow was between 357 to 473 liters per hour and the solution flow rate between 4 ml/min and 9 ml/min. The product was collected in a high performance cyclone. The resulting solid (14.7 g) has a purity of 98.6% (HPLC on area), with a content of 4-epimer of 0.80% in area.

The HPLC chromatogram of spray dried tigecycline is presented in FIG. 7

The HPLC details were as follows: Column: Luna C8 5 um, 250×4.6 mm; temperature: 30° C.; isocratic; moving phase: 0.05M KH2PO4+10 ml Triethylamine/L+H3PO4 until pH 6.2: CH3CN+0.5 g NaEDTA (80:20); wave length: 250 nm.

The invention claimed is:

1. A process for isolating amorphous tigecycline which process comprises the step of spray drying a solution of tigecycline in a solvent at a drying temperature of from about 70° C. to about 90° C., and wherein the isolated amorphous tigecycline shows an hygroscopic behavior characterized by an uptake of water equal or less than 2.9% w/w water in an environment with 45% relative humidity and equal or less than 22.9% w/w water in an environment with 95% relative humidity.

2. A process according to claim 1 wherein the solvent comprises water.

3. A process according to claim 1 wherein the solvent comprises an organic solvent.

4. A process according to claim 3 wherein the organic solvent comprises dichloromethane or ethyl acetate or both.

5. A process according to claim 1, wherein the concentration of tigecycline in the solution (w/w) is from 2% to 28%.

6. A process according to claim 5 wherein the concentration of tigecycline in the solution (w/w) is from 8% to 22% preferably at 10%.

7. A process according to claim 1, wherein the spray drying is aseptic spray drying.

8. A process according to claim 1, wherein the tigecycline has an HPLC purity of at least 98.5%.

9. A process according to claim 1, wherein the tigecycline comprises less than 1% of its C-4 epimer.

10. A process according to claim 1, wherein the tigecycline shows a glass transition temperature equal to or more than 129° C.

* * * * *